United States Patent [19]
Calvert et al.

[11] Patent Number: 6,092,522
[45] Date of Patent: *Jul. 25, 2000

[54] POWDER INHALER HAVING CAPSULE HOLDING STRUCTURE AND ANTI-STATIC WALLS

[75] Inventors: John Richard Calvert; Robert Stanley Cook; Michael Anthony Hobbs; Ann-Marie Leighton; Gordon Thomas Simpkin; Roy Trunley; Anthony Douglas West, all of Dagenham, United Kingdom

[73] Assignee: Rhone-Poulenc Rorer Limited, West Malling, United Kingdom

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/608,880

[22] Filed: Feb. 29, 1996

Related U.S. Application Data

[63] Continuation of application No. 07/965,385, filed as application No. PCT/GB91/00958, Jun. 14, 1991, Pat. No. 5,522,383.

[30] Foreign Application Priority Data

Jun. 14, 1990 [GB] United Kingdom .................... 9013261
Mar. 28, 1991 [GB] United Kingdom .................... 9106612

[51] Int. Cl.[7] ..................................................... A61M 15/00
[52] U.S. Cl. ................................. 128/203.21; 128/203.15
[58] Field of Search .......................... 128/203.15, 203.21, 128/203.12; 604/58

[56] References Cited

U.S. PATENT DOCUMENTS

5,522,383  6/1996  Calvert et al. ..................... 128/203.15

Primary Examiner—Aaron J. Lewis
Attorney, Agent, or Firm—Ross J. Oehler; Irving Newman

[57] ABSTRACT

An inhaler for inhaling pulverulent medicament from within a capsule comprises a chamber 24 within which the capsule is free to rotate while having its longitudinal axis in the median plane of the chamber and thus generally parallel to the front and rear walls 30 and 31 of the chamber, by virtue of the fact that the spacing between said front and rear walls is less than the axial length of the capsule but just greater than the diameter of the capsule. The device includes pins 21 serving as opening means to pierce the ends of the capsule while it is seated in a recess 25, whereupon the retraction of the pins 21 allows the capsule to be entrained into swirling airflow in the chamber 24 during inhalation of air through air inlets 26 and out through a mouthpiece nozzle 27.

16 Claims, 7 Drawing Sheets

POWDER INHALER HAVING CAPSULE HOLDING STRUCTURE AND ANTI-STATIC WALLS

This is a continuation of application Ser. No. 07/965,385 filed on Feb. 16, 1993, now U.S. Pat. No. 5,522,383, and International Application GB91/00958 filed on Jun. 14, 1991 and which designated the U.S.

FIELD OF THE INVENTION

The present invention relates to an inhaler for the inhalation of a medicament, usually pulverulent, from a capsule.

BACKGROUND OF THE INVENTION

Various forms of inhaler are already known, and among these are the ones in which the capsule is pierced, usually at the ends, in order to allow the medicament to be withdrawn during inhalation, and those in which the cap portion of the capsule is removed from the body portion in order to allow the medicament to be extracted.

Extraction of the medicament usually occurs as a result of the inhaled airstream passing over or through the capsule.

With both of the above types of inhaler, it is known to allow the airstream passing through the inhaler to adopt a vortical configuration which results in the pierced capsule or the separated capsule cap and body portions tumbling in the airstream.

It is a disadvantage of virtually all of the known inhalers that not all of the medicament is withdrawn from the capsule or the separated capsule cap and body portions, and this is frequently because the capsule portions or the capsule as a whole can become lodged in the inhaler in a position where either the extraction effect of the inhalation air is unable to operate effectively or the capsule or capsule cap and body portions can become prevented from tumbling freely by a mechanical constraint.

SUMMARY OF THE INVENTION

It is an object of the present invention to provide an inhaler in which the disadvantages mentioned above are eliminated.

In accordance with one aspect of the present invention there is provided an inhaler which comprises a chamber defined by (a) first and second generally parallel spaced opposed walls defining a median plane of said chamber mid-way therebetween, and between which parallel spaced walls the capsule can fit with its longitudinal axis generally parallel to said first and second walls but in any angular orientation, and (b) at least one peripheral wall; an exhaust nozzle through which air can be exhausted from said chamber by inhalation; at least one air inlet arranged in relation to the exhaust nozzle to generate in the chamber during inhalation an airflow rotating about an axis generally perpendicular to said first and second walls; and holding means in the inhaler in association with means operable from outside the closed chamber for opening a capsule while held in the holding means with the longitudinal axis of the capsule perpendicular to said axis, wherein the holding means are effective to hold a capsule having a length greater than the minimum spacing between first and second walls and less than the minimum cross-sectional dimension of said chamber when viewed parallel to said axis of rotation and is configured to hold a capsule with its axis of symmetry substantially coincident with the median plane of said chamber, and to hold a capsule having a diameter less than said minimum spacing between the first and second walls.

A second aspect of the present invention provides an inhaler which comprises a chamber defined by (a) first and second generally parallel spaced opposed walls between which the capsule can fit with its longitudinal axis generally parallel to said first and second walls but in any angular orientation, and (b) at least one further wall; an exhaust nozzle through which air can be exhausted from said chamber by inhalation; at least one air inlet arranged in relation to the exhaust nozzle to generate in the chamber during inhalation an airflow rotating about an axis generally perpendicular to said first and second walls; and a recess in the inhaler in association with means for opening a capsule while held in the recess with the longitudinal axis of the capsule perpendicular to said axis, wherein the opening means are effective to open a capsule having a length greater than the minimum spacing between said first and second walls and less than the minimum cross-sectional dimension of said chamber when viewed parallel to said axis of rotation, and to open a capsule having a diameter less than said minimum spacing between the first and second walls; and wherein the chamber is non-circular and is able to allow the capsule to rotate freely about its transverse axis under the influence of the inhaled airstream and to impact against said at least one further wall in order to increase the likelihood of ejection of the medicament from within the capsule.

A third aspect of the invention provides an inhaler comprising a mouthpiece; and a swirling chamber to receive a container which can be agitated, when open, in an inhalation airstream to release powdered medicament from the interior of the container; wherein the chamber has walls defined of an anti-static member having a surface resistivity of less than $10^{12}$ Ohms.

BRIEF DESCRIPTION OF THE DRAWINGS

In order that the present invention may more readily be understood the following description is given, merely by way of example, reference being made to the accompanying drawings, in which.

DESCRIPTION OF PREFERRED EMBODIMENTS

Figure 1:
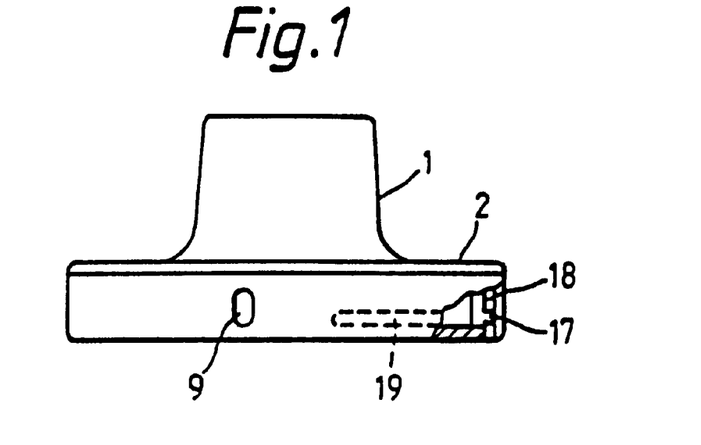
FIG. 1 is a side elevational view of an inhaler in accordance with the present invention.
Figure 2:
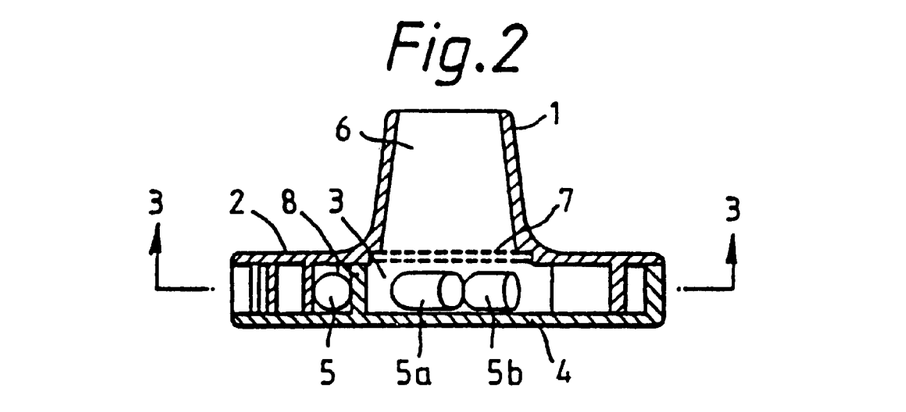
FIG. 2 is a transverse sectional view of the inhaler of FIG. 1.

Referring now to the drawings, FIG. 1 shows a mouthpiece nozzle 1 on a plate 2 forming one wall of a capsule-emptying chamber 3 (FIG. 2).

The opposite wall of the chamber 3 is defined by a rear casing panel 4 which is removable in order to allow a capsule 5 to be inserted into the inhaler ready for opening. The two parts of the device are held together by means of a bayonet system to be described later.

In register with the air passage 6 centrally within the mouthpiece nozzle 1 is a grid 7 which is preferably antistatic by virtue of a high electrical conductivity and/or low surface resistivity, and/or high surface electrostatic dissipativity, through which grid the inhalation air passes but through which fragments of the capsule casing are unable to pass, and hence unable to enter the respiratory tract of the user.

FIG. 2 shows an important characteristic of the present invention in that the cross-section of the capsule 5 is only slightly smaller than the minimum spacing between the planar right hand chamber wall (defined by the panel 2 and the screen 7) and the planar left hand chamber wall (defined by the rear casing panel 4) with the result that both the capsule body 5a and the capsule cap 5b are prevented from adopting any other orientation than one in which their axes of symmetry are parallel to the planes of the left hand and right hand chamber walls.

It will of course be appreciated that the chamber 3 is defined not only by the left hand and right hand walls 4 and 7, respectively, but also by transversely extending walls such as the partition 8 shown in FIG. 2.

FIG. 1 illustrates an air inlet 9 which is one of several such inlets of the inhaler.

Figure 3:
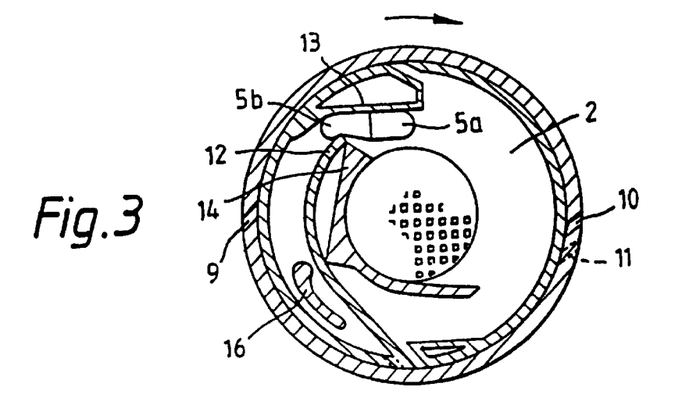
FIG. 3 is a sectional view taken on the line 3—3 of FIG. 2, with the capsule in position ready for opening by the opening means.

FIG. 3 shows a sectional view taken on the line 3—3 of FIG. 2, and illustrates not only the above-mentioned air inlet opening 9, but also two further air inlets 10 and 11, the functions of which will be described below.

FIG. 3 again shows the capsule 5 in position ready for opening, with the capsule cap portion 5b held between an arcuate baffle 12 and an anvil 13. Alternatively the capsule could be positioned in the same manner except that the body portion 5a is squeezed between the baffle 12 and anvil 13 and the cap portion 5c will be removed by a knife 14 (FIG. 4).

In this position the capsule 5 has its longitudinal axis in the median plane of the chamber, i.e. the plane perpendicular to the axis of symmetry and located mid-way between the panels 2 and 4. The capsule is inserted into this position by sliding in a direction perpendicular to the plane of the paper of FIG. 3, either with the rear casing panel 4 removed from the rest of the inhaler or by insertion through an optional insertion port to be described below with reference to FIG. 6.

FIG. 3 also shows a capsule holding anvil 13 moulded integrally with the mouthpiece panel 2. Likewise, the arcuate baffle 12 is integrally moulded with the panel 2.

Figure 4:
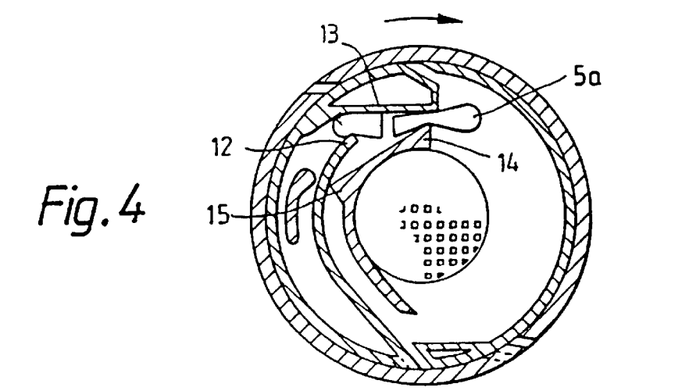
FIG. 4 is a view similar to FIG. 3 but showing the inhaler slightly later during the operating cycle in which the capsule has just been opened.

Rotatable relative to the arcuate baffle 12, by virtue of being moulded integrally with the rear casing panel 4, is an opening knife 14 which rotates in the clockwise direction during operation of the inhaler from the loading configuration to the inhalation configuration, so as to flick the capsule body portion 5a away from the cap portion 5b, as shown in FIG. 4 at the instant of separation of the capsule portions 5a and 5b.

Figure 5:
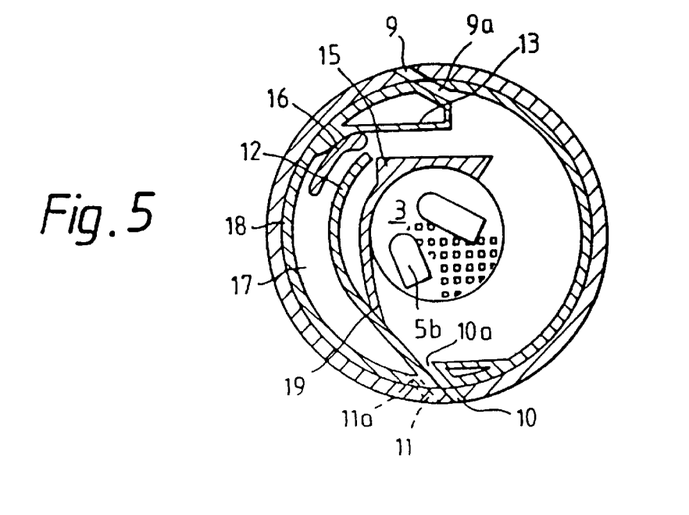
FIG. 5 is a view, again similar to FIG. 3, but this time showing the two separated capsule portions in the chamber being tumbled to remove the contained medicament.

Behind the opening knife 14 is a guide member 15 which, at the instant when a capsule ejector 16 also carried by the rear casing panel 4 ejects the capsule cap portion 5b from between the baffle 12 and the anvil 13, as shown in FIG. 5, cooperates with the anvil 13 to define a passage along which the portion of the capsule which has just been ejected from between the anvil 13 and the baffle 12 must pass towards the inhalation chamber 3. This guiding action prevents the ejected capsule portion from being jammed. It will also be appreciated that the trailing wall 19 on which the guide member 15 is formed also provides a near seal with the baffle 12, having the result that the majority of the inhalation air sweeps generally tangentially into the chamber 3 by way of the inlet orifices 9 and 10, although the additional air inlet orifice 11 does allow a purge stream to pass along an arcuate passage 17 between the arcuate baffle 12 and an outer wall 18 of the inhaler, in order to purge the spacing between the baffle 12 and the anvil 13 of any medicament which may have been spilt there as a result of the opening operation. The existence of this purge stream through the air inlet 11 therefore further enhances the degree of emptying of the medicament from the inhaler as a whole. The various inlets 9, 10 and 11 thus contribute to the creation of a vortical airflow in the chamber 3.

It will of course be appreciated that there are three important criteria of the device in accordance with the present invention:

(i) the pressure drop across the loaded inhaler, between inlet 9 or 10 and the inhalation mouthpiece 1 should be as low as possible;

(ii) there is a need for as near perfect as possible delivery of the medicament from within the capsule in order to allow the medicament to enter the inhalation airstream; and (iii) there is equally a need for as high as possible a degree of emptying of the device as a whole, because the efficiency of delivery of the medicament depends not only upon the medicament being removed from the capsule but also upon the medicament actually reaching the respiratory tract of the user during inhalation.

The final position, shown in FIG. 5, when the inhaler is in the relative rotational positioning of its two major parts where the capsule has been opened and released into the spinning chamber 3 for capsule emptying, is the only one in which the various air inlets 9, 10 and 11 all communicate with the interior of the device by means of the corresponding inlet gaps 9a, 10a and 11a respectively. In all other positions they are closed in that the ports are not aligned until the capsule has been opened.

Figure 6:
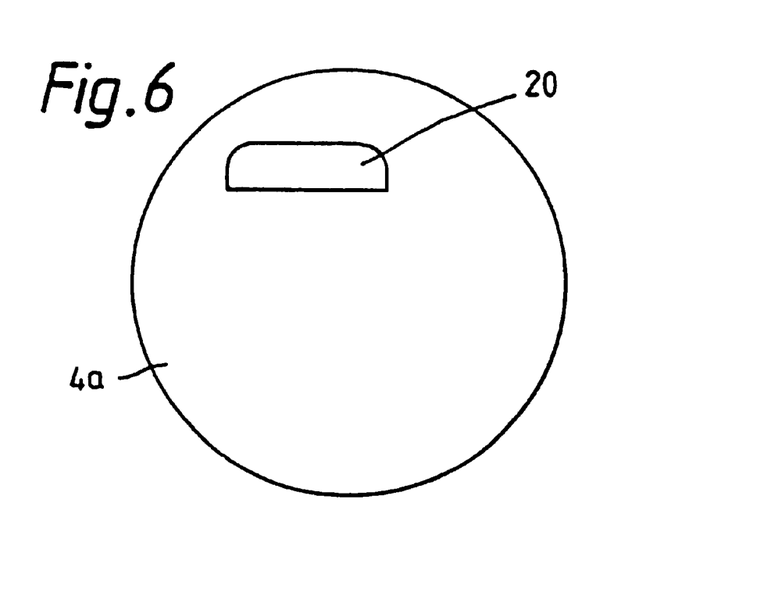
FIG. 6 is an underneath plan view showing the rear casing, with an optional hinged cover to facilitate loading of a capsule to be opened.

FIG. 6 shows an alternative embodiment of the device in which the rear casing panel 4a includes a capsule insertion port with a hinged or push fit cover 20 which can be opened to facilitate insertion of a capsule 5 in order to allow the device to be loaded without the need to separate the mouthpiece 1 and its panel 2 from the rear casing panel 4. However, these portions will nevertheless normally need to be separated at the end of the operating cycle in order to allow the spent capsule body and cap portions to be removed and permit cleaning of the device by the user.

The bayonet system, mentioned above, for holding the two parts of the device together comprises a pin 17 on the exterior of the skirt of the mouthpiece member engageable in an axially extending slot 18 (FIG. 1) in the skirt of the rear panel part. This slot opens into a groove 19 running round the skirt of the rear panel over approximately 80° of arc of the rear panel part, so as to permit rotation of the rear panel part relative to the mouthpiece part without axial separation of these two parts.

In order to minimise the extent to which the released powdered medicament can agglomerate on the surface of the air passage through the inhaler, the panels 2, 4 and the partition 8 which define the chamber portion 3 may be formed of a polymer with a low surface resistivity, thereby having anti-static properties. Preferably the material defining the inside wall of the chamber 3 is a polymer having a surface resistivity less than $10^{12}$ Ohms or more preferably less than $10^8$ Ohms. In the present embodiment, the entire device is formed of the same polymer of low surface resistivity, but if desired the chamber-defining walls may be provided with an inner lining of the polymer of low surface resistivity.

There are various additives known to increase the anti-static properties of polymers, for example by increasing the electrical conductivity or reducing the surface resistivity, or enhancing the static dissipativity properties. One possibility is to incorporate carbon or steel filler, often in the form of fibres, into the polymer used for manufacture of those components to be given enhanced anti-static properties. This enhances the electrical conductivity and/or lowers the surface resistivity. Alternatively non-fibrous chemical additives, often blended into the moulding polymer in chip form prior to the moulding process, may be used to lower the surface resistivity in the moulded product. The product PEBAX manufactured by the company Atochem of France is a polyether block amide product which may be obtained in an anti-static grade by use of such additives. Alternative materials for this application include the ATMER range of polypropylenes, containing antistatic additives, manufactured by ICI.

Another possibility is for the moulded component to be coated with an electrically conducting layer which thus reduces the surface resistivity.

Preferably the surface resistivity is less than $10^{12}$ Ohms, and more preferably it is less than $10^8$ Ohms.

More preferably the mouthpiece in any of the embodiments may have at least its inner wall formed of such a polymer of low surface resistivity.

As with the embodiments to be described below, the embodiment of FIGS. 1 to 6 is formed by injection moulding. The above-mentioned polymeric material of low surface resistivity is itself capable of injection moulding to form the relevant parts of the device, or the whole of it.

Figure 7:
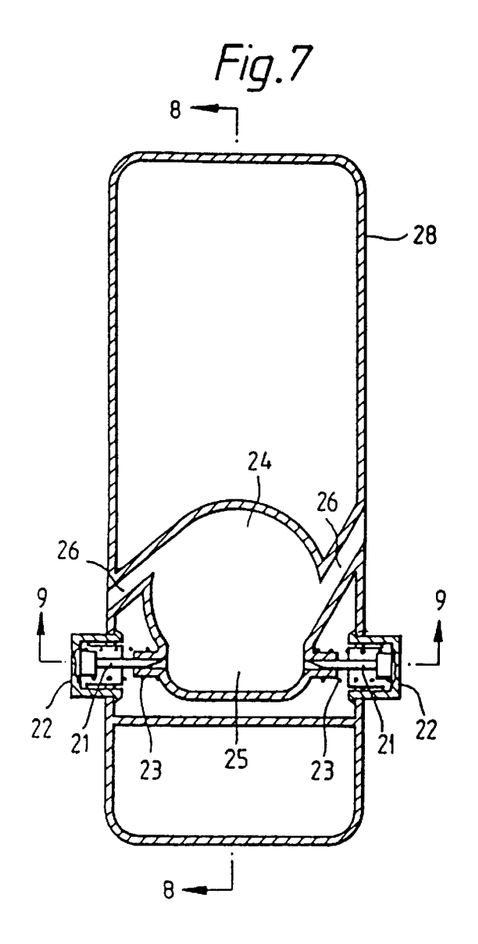
FIG. 7 is a sectional view of an alternative embodiment of inhaler of the pin-piercing type.

Turning now to FIG. 7, there will be seen an alternative embodiment of the inhaler in accordance with the present invention in that in this case the capsule is not opened by separation of its cap and body portions, but is instead pierced by pins in order to allow extraction of the contents by a combination of pneumatic action, centrifugal action, and impact of the pierced capsule with the lateral wall of the swirling chamber.

FIG. 7 shows two capsule piercing pins 21 operated by respective buttons 22 which are biased outwardly by means of helical compression springs 23.

For this purpose the chamber 24, having a peripheral wall 24a adjoining flat end walls defined by a grid 30 and a wall of a plug 29 to be described below, also has in its peripheral wall a recess 25 defined by a bulge 25a in the wall 24a able to accommodate the capsule while it is in the median plane of the relatively flat chamber.

Figures 8, 9:
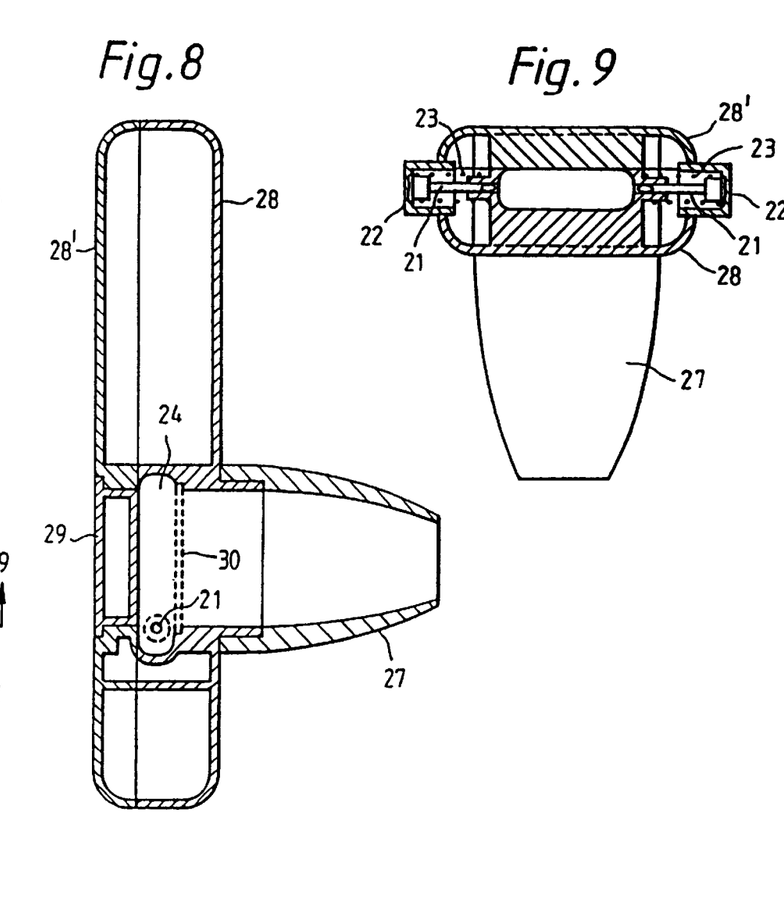
FIG. 8 is a sectional view of the inhaler of FIG. 7, taken on the line 8—8 of FIG. 7.
FIG. 9 is a sectional view taken on the line 9—9 of FIG. 7.

The chamber furthermore includes two air inlets 26 which clearly generate a swirling motion in the chamber, about an axis which is generally centrally of the main chamber and extends perpendicular to the plane of the paper in FIG. 7, as air is aspirated through the mouthpiece nozzle 27 shown in FIG. 8 and 9.

The operation of the inhaler shown in FIGS. 7, 8 and 9 is relatively straightforward and is as follows.

Firstly, the inhaler is opened by separating the right hand body portion 28 from the left hand body portion 28' shown in FIG. 8, so that a capsule can be inserted in the recess 25 of the chamber 24.

The push-buttons will at this stage be biased to their outward positions so that the two needles 21 are retracted from the capsule-receiving bulge 25a in the chamber wall.

The device is then re-assembled by joining the body portions 28 and 28' in the FIG. 8 configuration, with some detent means (not shown) in order to hold the two halves together in the assembled configuration.

Up to now the capsule is closed and the operator does not have to fiddle with either a pierced capsule or a capsule whose cap portion has been separated from its body portion.

The operator then simply squeezes the two push-buttons 22 inwardly, in order to cause the needles 21 to rupture the ends of the capsule in the recess 25, and then to release those push-buttons so that they can be biased outwardly again by the compression springs 23. The capsule is then free in the recess 25 ready for entrainment when inhalation starts.

The user then simply inhales through the mouthpiece 27 of FIGS. 8 and 9 to generate the necessary swirling airstream into the chamber 24 through the inlets 26, and this same swirling action will detach the capsule from the recess 25 in which it is a loose fit, and will cause the capsule to rotate rapidly about the above-mentioned axis of rotation of the vortical swirling airflow in the chamber 24.

The fact that the capsule is of a length shorter than the diameter of the chamber 24 means that it is able to be spun around its transverse axis in the vortical airflow, and yet at the same time because its length is nearly equal to that diameter it is able to contact the peripheral wall of the chamber 24 so as to sustain impacts which remove the pulverulent medicament from within the capsule by a percussive action.

This degree of impact with the walls of the chamber 24 is enhanced by the presence of the recess 25 which gives the chamber 24 a generally non-symmetrical or eccentric appearance, resulting in random and rapidly occurring impacts which augment the centrifugal emptying of the spinning capsule shell.

When the inhalation is complete, the medicament will almost completely have been emptied from the capsule, and indeed from the chamber 24 by being exhausted through the air-pervious grid 30 defining one of the opposed flat walls of the chamber 24 (the other wall being defined by a closure plug 29).

The inhaler can then either be opened immediately in order to remove the spent capsule, or opened only when the next inhalation is to be carried out.

Provided the inhaler is kept dry, and if the material chosen for all of the embodiments of the inhaler in accordance with the invention is one which has relatively low electrostatic attraction for the powder in the capsule, the inhaler will not need regular cleaning when used by the same patient (i.e. other than for considerations of hygiene).

Figure 10:
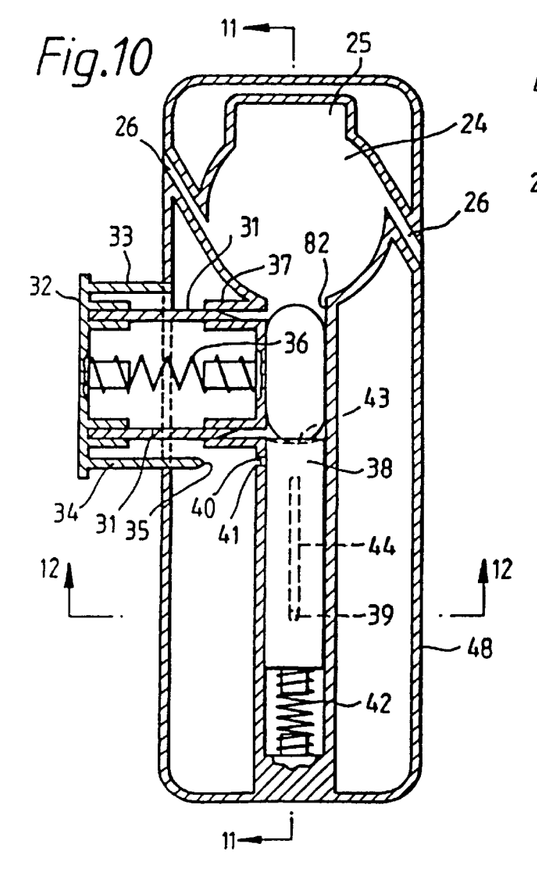
FIG. 10 is a sectional view of a third embodiment of inhaler.
Figures 11, 12:
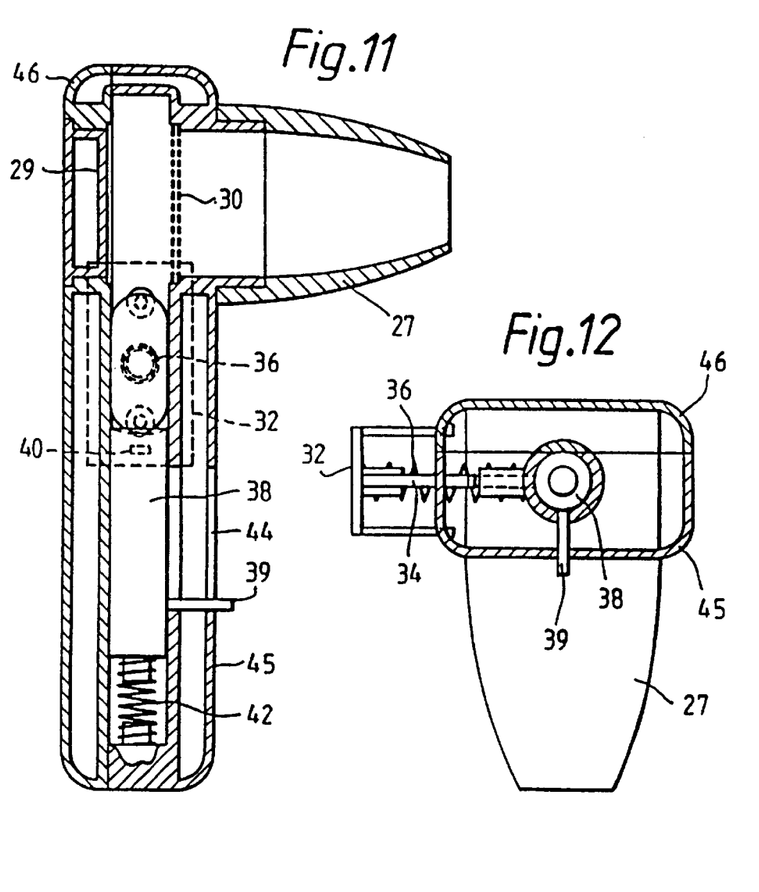
FIG. 11 is a sectional view taken on the line 11—11 of FIG. 10.
FIG. 12 is a sectional view taken on the line 12—12 of FIG. 10.

The embodiment of FIGS. 10, 11 and 12 is similar in many ways to that of FIGS. 7, 8 and 9 but differs in the means for opening the capsule.

Those components of the device of FIGS. 10, 11 and 12 which correspond identically to those of FIGS. 7, 8 and 9 are denoted by the same reference numerals and will be described only briefly, if at all, in the following description.

FIG. 10 shows that the capsule, in its opening position, is now aligned with a diameter of the chamber 24, but still has its longitudinal axis in the median plane of the chamber 24, i.e. in the plane which lies mid-way between the planar front and rear walls of the chamber as viewed in FIG. 10 (the left hand and right hand walls as viewed in FIG. 11). Again, the planar left hand wall is formed by a separate plug 29, and the planar right hand wall 30 is formed by a grid which serves to prevent the capsule and/or any fragments released upon perforation by the opening pins, from entering the respiratory tract of the user during inhalation. In the present embodiment the grid 30 is of a material which is electrically conductive or is otherwise anti-static. Preferably the material used is a conductive polymer. However, the grid may be of a metal such as stainless steel.

In this embodiment the pins 31 for opening the capsule are carried by a single push-button assembly 32 which is guided by a guide peg 33 and an extended guide peg 34 the end of which has a small diameter extension 35 to act as a latch release as will be described shortly.

Again a compression spring 36 is provided in order to bias the push-button 32 to its outward position in which the two pins 31 are retracted from their respective guide ducts 37.

In order to allow the capsule to enter its opening recess, in which position it is illustrated in FIG. 10, an ejector slide 38 is mounted centrally within the body of the inhaler and is slidable axially under the control of an operating handle 39 (FIG. 11). In order to hold the ejector in the retracted position shown in FIG. 10, it includes a latch pip 40 which engages in an aperture 41 where it remains until ejected by the small diameter extension 35 serving as the latch release portion of the guide pin 34 for the push-button 32. Once the latch has been released, a compression spring 42 urges the ejector axially along the body of the inhaler to eject the capsule from the diametrically extending recess into the main chamber 24, and at the same time the end-of-travel position of the ejector 38 is such that a concave arcuate leading surface 43 of the ejector fits flush with the peripheral wall of the chamber 24 in order to ensure that the capsule will not be able to re-enter that capsule-opening recess during subsequent tumbling in the vortical airstream upon inhalation. It will however impact against the edges of a recess 25 which in this embodiment serves only to provide an irregularity to the peripheral wall of the swirling chamber to provoke ejection of the powdered medicament from the capsule by percussive action.

FIG. 10 shows, in broken lines, the location of a slot 44 (see also FIG. 11) in the front casing 45 of the inhaler, to allow the operating handle 39 of the ejector 38 the degree of travel required for movement between the capsule-accepting position shown in FIG. 10 and the capsule-ejecting position (which is not shown in the drawings). It should be noted that the plane of section for FIG. 11 is taken centrally of the slot 44.

The operation of the device shown in FIGS. 10, 11 and 12 will now be described.

Firstly the operating handle 39 of the ejector 38 is drawn to the position shown in FIGS. 10 and 11, in order to free the capsule-opening recess.

Then the front body portion 45 is removed from the rear body portion 46 of the inhaler in order to allow insertion of the capsule into the capsule-opening recess.

The two body portions 45 and 46 are then fastened together again to close the chamber 24 ready for the capsule-opening operation.

It will of course be appreciated that throughout the above three operations the push-button 32 is held in its extended position shown in FIG. 10, by virtue of the compression spring 36.

The push-button 32 is now inserted in order to drive the two pins 31 into the capsule ends, and at the end of that insertion stroke the latch release extension 35 of the guide pin 34 will contact the latch pip 40 to release the latch and allow the ejector 38 to be driven forwardly to eject the capsule, under the action of the compression spring 42.

With the capsule now positioned in the chamber 24, the user places his or her lips over the mouthpiece nozzle 27 and inhales in order to generate the swirling motion airstream within the chamber 24, giving rise to ejection of the medicament from within the capsule, by the three-fold actions of pneumatic suction, centrifugal flinging, and percussive impact with the peripheral walls 24*a*, 25*a* of the chamber 24.

The user has an indication that the capsule has been fully opened by the piercing operation in that unless the push-button 32 is inserted fully, to a position which will correspond to adequate rupturing of the capsule ends by the needles 31, the latch release extension 35 of the pin 34 will not displace the latch pip 40 from its aperture 41 and hence the ejector will not be released to eject the capsule. The user will be aware of this by the fact that the operating handle 39 of the ejector 38, also serving as an indicator, will not have displaced from the position shown in FIGS. 10 and 11. Only when this indicator has moved in order to signal ejection of the capsule should the operator embark on the inhalation step.

Although in the above description it has been indicated that the embodiments of FIGS. 7 to 9 and FIGS. 10 to 12 both rely on separation of the front and rear body portions in their entirety in order to allow insertion of a new capsule (and, incidentally, removal of the spent capsule from the last use), it will of course be understood that other arrangements are possible.

In FIGS. 10 to 12, the body portion 46 may only extend down as far as the end of the inhalation chamber nearest the capsule opening means 31–34.

Alternatively, in both embodiments of pin opening device (FIGS. 7 to 9 and FIGS. 10–12), the plug 29 or the mouthpiece 27 and grid 30 section shown can be made to be removed in order to provide for access to the chamber 24 to allow removal of the spent capsule and equally insertion of a fresh capsule in either the capsule-opening recess 25 of FIG. 7 or the capsule-opening recess in which the capsule is shown as being positioned in FIG. 10. For this purpose the plug 29 or the mouthpiece and grid section may be provided with any suitable means for enabling it to be removed, and the design of such means will be within the capability of the skilled expert in the art. Possibilities include screw threading on the plug 29 and the recess into which it fits, or a hinge, for example a thin film hinge, to attach the plug 29 to the body of the inhaler.

It will be appreciated that each of the three embodiments described in the present application has the feature of the capsule being opened in the inhaler, while oriented with its major axis in the median plane of the chamber in which the swirling inhalation airflow will cause the capsule to tumble to discharge its contents. In the embodiment of FIGS. 1 to 6 this opening operation relies on physical separation of the capsule body from the capsule cap while positioned to one side of the chamber, in a position almost tangential to the airflow which is generated during inhalation; in the embodiment of FIGS. 7 to 9 the opening position is again almost tangential to the airflow in the chamber, but opening is effected by axially moving penetrating pins at each end of the capsule; and in the embodiment of FIGS. 10 to 12 the capsule is positioned diametrally of the chamber and opening is effected by transverse (i.e. radial) movement of pins but again operating at each end of the capsule.

It will be appreciated that in the embodiments of FIGS. 7 to 9 on the one hand and FIGS. 10 to 12 on the other hand, although the capsule is opened by penetration at each end there is no question of airflow having to pass directly through the capsule as the sole means of removing the pulverulent contents. The development of the present invention has revealed that such a system would give too high a pressure drop across the inhaler during the inhalation operation for a person with a disability of the respiratory function to inspire the contents efficiently, and bearing in mind that the capsule inhalation treatment is intended for those with some disability of the respiratory function it is important to keep the pressure drop at a minimum, while aiming for as near as possible total removal of the contents during the inhalation. The present invention achieves such high efficiency of removal of the medicament from not only the capsule but also the inhalation device as a whole, by (i) allowing random impact of the capsule ends with the walls of the chamber, and by (ii) ensuring that the axis of symmetry of the capsule or of the individual separated capsule cap and body parts during the tumbling operation remains generally parallel to the median plane of the chamber so as to give the best possible centrifugal action, and equally the optimum pneumatic suction on the interior of the capsule, during the inhalation operation. If the capsule were able to tumble into a different orientation where the axis of symmetry becomes anything other than parallel to the median plane of the chamber, the degree of suction will be attenuated, or at least less reliable in strength. It is a feature of the inhalers disclosed in the present application that the contents of the capsule can be efficiently entrained in the airstream even at the relatively low airflow rates likely to be associated with users with impaired respiratory functions.

There are various alternative possibilities for the configuration of the chamber, and it is felt that the adoption of a chamber in which the shape is not fully cylindrical as shown in FIG. 10 is preferable in that this will give rise to an increased likelihood of percussive impact on the walls of the recess 25 to tap the contents of the capsule clear of the ruptured capsule shell and capsule body and cap portions.

For the embodiments of FIGS. 7 to 9 and 10 to 12 it is desirable for the axial length of the chamber 24 (the minimum spacing between the front and the rear flat walls of the chamber) to be less than the axial length of the capsule, and preferably less than it by a margin sufficient to ensure that there is no likelihood of the capsule being trapped in an inclined position. For the embodiment of FIGS. 1 to 6 it is preferable for the axial length of the chamber to be less than the axial length of the cap portion (this being shorter than the body portion) of the capsule, for the same reason.

There are known inhalers using recesses formed in the opposed walls which have been described herein as the front and rear walls of the chamber, where the capsule is held clear of the median plane of the chamber during capsule opening, or is even inserted in a capsule-opening recess with the longitudinal axis of the capsule parallel to the axis of rotation of the swirling airflow during inhalation. Those constructions may result in a possibility for the capsule to become lodged in the capsule opening recess during the tumbling action, with the resultant holding of the capsule and impeding of the capsule-emptying action during inhalation. It is considered an important optional feature of the present invention that the front and rear walls of the chamber are generally flat without such depressions, so that the likelihood of the capsule becoming caught during inhalation is reduced if not negligible.

For the same reason the ejector 38 has the concave leading surface 43 which closes off the capsule-opening recess, thereby removing the possibility of the rounded ends of the capsule becoming caught against the sharp edges of the capsule-opening recess, leading to the likelihood of the capsule jamming during inhalation.

As indicated above, the material used for the walls defining at least the swirling chamber, and preferably also the mouthpiece, may in all embodiments of the inhaler in accordance with the present invention be one which is not likely to generate a high electrostatic charge which would cause the released pulverulent medicament to adhere to the surface of the body of the inhaler rather than passing outwardly through the mouthpiece nozzle.

Figure 13:
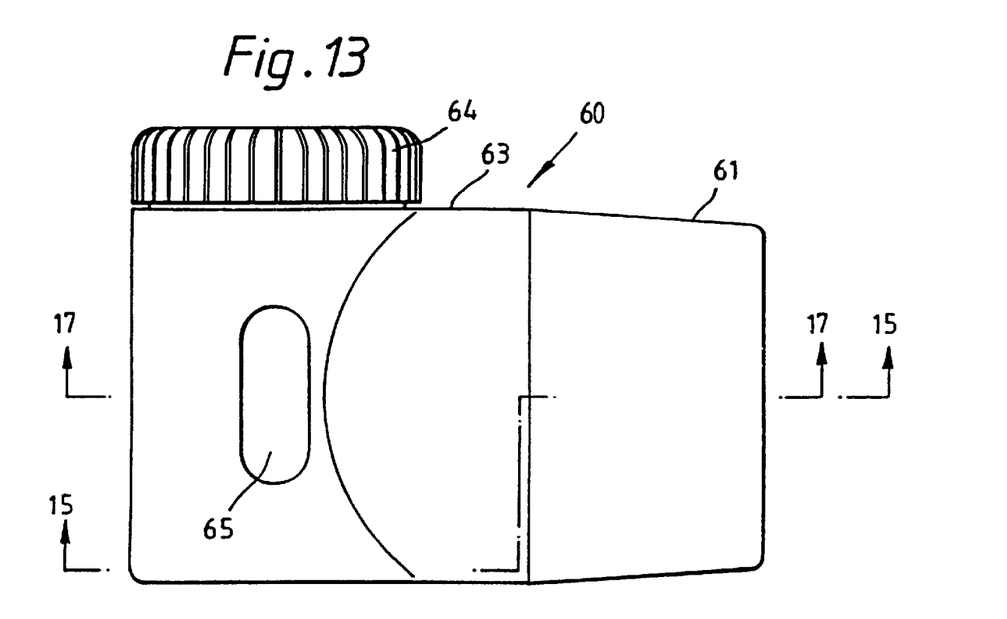
FIG. 13 is an elevational view of a further embodiment of inhaler in which the capsule is pierced by opening pins.

FIG. 13 shows a further embodiment of inhaler in which the capsule is to be opened by piercing with pins at its ends. This inhaler 60 has the mouthpiece 61 in the preferred embodiment hinged at 62 to the body portion 63 in which the inhalation chamber and the capsule opening means are defined. Alternative means of detaching the mouthpiece from the body of the inhaler may be employed; for example, unscrewing, or twisting by means of a bayonet pin or pins and arcuate slot may be provided for.

The capsule opening means is rotary in action and comprises a rotor having a recess 69 (FIG. 15) to receive the capsule to be opened and a pusher member to eject the pierced capsule from the recess 69, and the rotor itself is driven by a disc-like control wheel 64 operated manually. In a first, capsule-receiving position (illustrated in more detail in FIG. 15) the capsule-receiving recess 69 in the rotor is in register with a capsule insertion opening 65 in the body 63.

Figure 14:
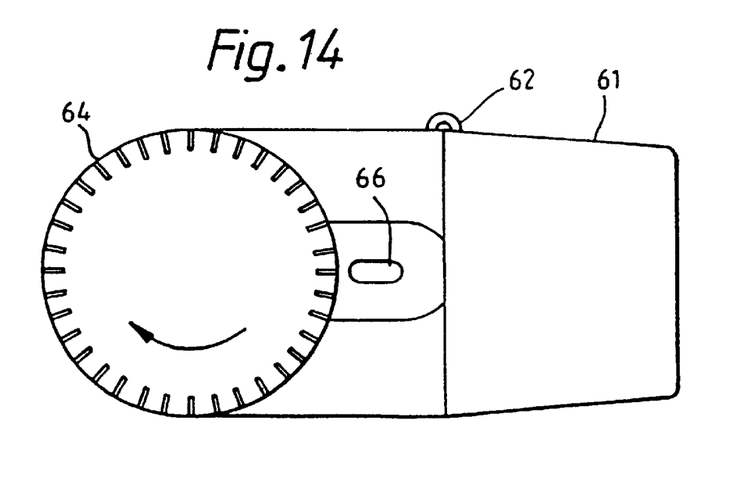
FIG. 14 is a top plan view of the device of FIG. 13.

The inhalation chamber is positioned at the right hand end of the body 63, close to the point of junction between the body and the mouthpiece 61, and one of the air inlet openings 66 to that inhalation chamber can be seen in FIG. 14.

Figure 15:
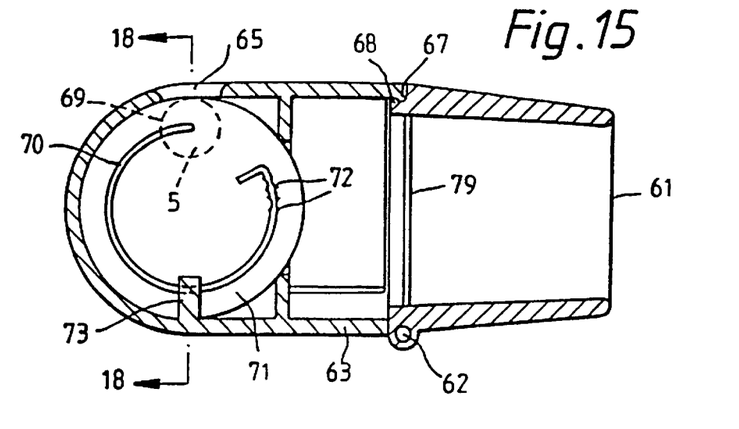
FIG. 15 is a section on the line 15—15 of FIG. 13, showing the device in the capsule-receiving configuration.

FIG. 15 is a sectional view taken on the line 15—15 of FIG. 13 and shows the mouthpiece clipped in its operative position by catch engagement between a projection 67 of the body and a corresponding projection 68 of the mouthpiece.

FIG. 15 also shows the capsule 5 in position in the capsule-receiving recess 69 in register with the capsule-inserting opening 65.

An arcuate wire clip 70 having a sharpened bent end portion coaxial with the capsule 5 is secured to the end of the rotor 71 by projections 72 which trap the wire clip to rotate with the rotor.

Figure 18:
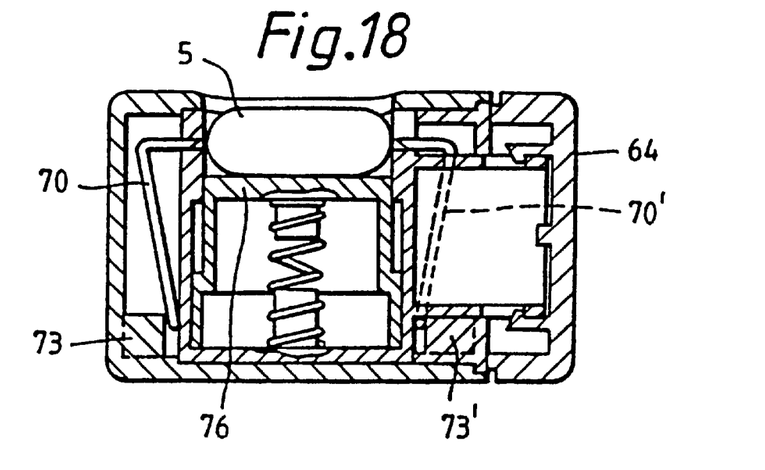
FIG. 18 is a section taken on the line 18—18 of FIG. 15.
Figure 19:
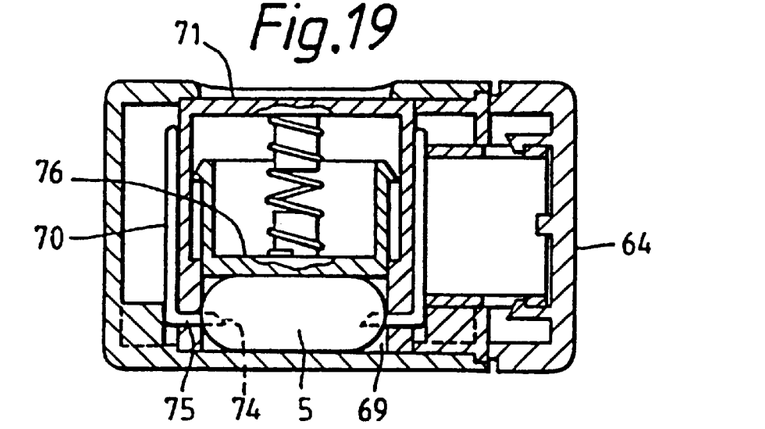
FIG. 19 is a section taken on the line 19—19 of FIG. 16.

A cam 73 cooperates with the wire 70 in a manner which will be more readily evident from FIGS. 18 and 19, to drive the bent end portion of the wire clip axially into the capsule 5 held in the recess 69 to pierce the capsule.

It will of course be appreciated that there are in fact two such wires 70, one at each end of the rotor 71.

Figure 16:
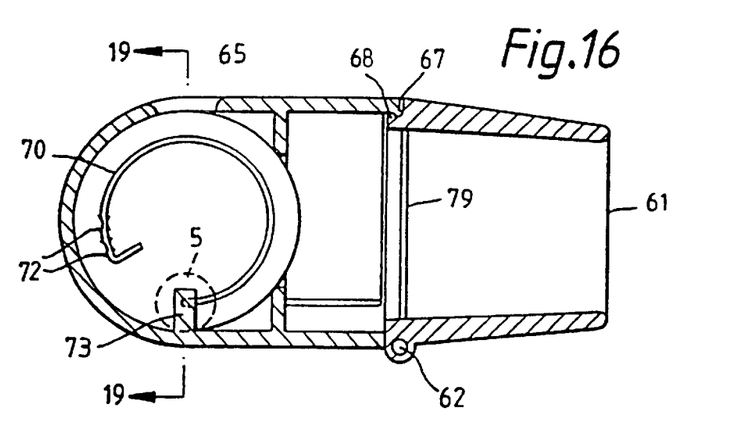
FIG. 16 is a view corresponding to FIG. 15 but showing the device in the configuration in which the capsule has just been ruptured.

FIG. 16 shows the rotor 71 after rotation in the anti-clockwise direction through 180° to bring the capsule 5 with its axis passing through the cam 73.

As shown in FIG. 19, in this position the sharpened end 74 of the bent portion 75 of the wire clip 70 has been pressed into the end of the capsule 5 by the operation of the cam 73 of the body 63 as the rotor 71 rotates.

Comparing FIGS. 18 and 19 will show that in the FIG. 18 "capsule-receiving" position the wire clip 70 is not flat against the rotor but is in fact helical relative to the rotor end wall and that as the rotor rotates towards the FIG. 19 position the point where the cam 73 bears against the back of the wire clip 70 gradually moves around the clip towards the bent end portion 75.

FIGS. 18 and 19 show that there is a similar cam 73' operating on the wire clip 70' at the opposite end of the rotor 71, in the same manner as described above for the cam portion 73.

Figure 17:
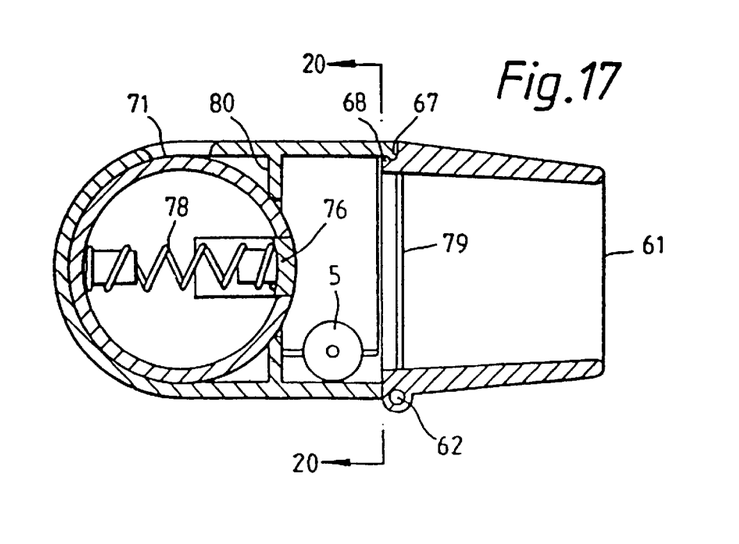
FIG. 17 is a section taken on the line 17—17 of FIG. 13 but when in the configuration in which the capsule has just been ejected into the inhalation chamber.

FIG. 17 is a sectional view taken on the line 17—17 of FIG. 13 and shows the pusher member 76 within the rotor 71 to eject the capsule 5 into the inhalation chamber 77 after a further 90° of rotation of the rotor 71.

This pusher member 76 is biased in a radially outward direction by means of a helical compression spring 78.

FIG. 17 also shows that, in common with the embodiments of FIGS. 1 to 6, 7 to 9 and 10 to 12, the inhalation chamber 77 is again defined by a generally flat right hand wall formed by the preferably electrically conductive grid 79 of the mouth piece 61 and a left hand wall 80 having an aperture through which a part of the circumference of the rotor 71 may project, but which is generally flat particularly when the capsule pusher member 76 is in the radially outermost position shown in FIG. 17.

The dimension of the inhalation chamber between and perpendicular to the two flat walls 80 and 79 is again less than the axial length of a capsule 5 but greater than the diameter of the transverse cross-section of the capsule 5.

Figure 20:
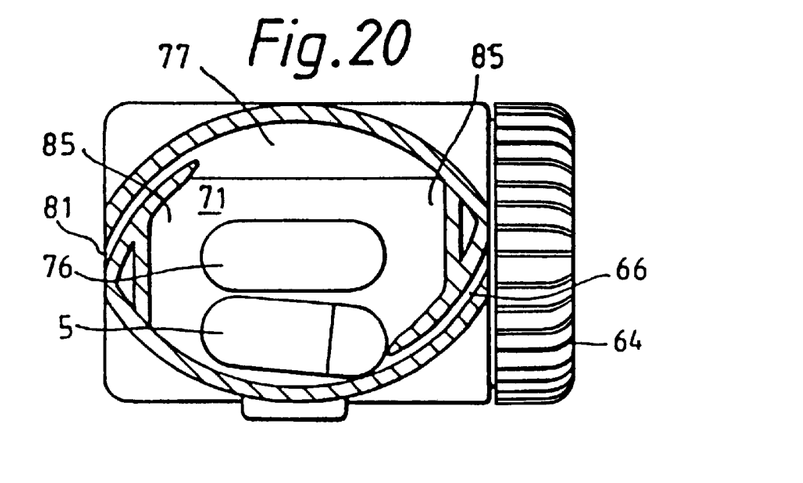
FIG. 20 is a section taken on the line 20—20 of FIG. 17.

The airflow pattern through the inhalation chamber 77 can be best appreciated from FIG. 20 which shows an inlet opening 81 entering the chamber 77 generally tangentially and the inlet opening 66 of FIG. 14 which also leads into an opening generally tangentially of the chamber 77.

FIG. 20 also shows the capsule pusher member 76 of the rotor 71 and the recesses 85 at opposite sides of the swirling chamber 77 to provoke percussive ejection of the medicament from the capsule.

In operation of the device shown in FIGS. 13 to 20, the operating disc 64 is first of all rotated to the FIG. 15 position with the inhalation chamber 77 clear of the debris of any previous capsule. This clearance of the chamber 77 can be achieved by swinging the mouthpiece 61 aside by means of the hinge 62.

The capsule 5 is then pressed through the insertion opening 65 and into the recess 69 against the action of the compression spring 78 and the disc 64 is then rotated firstly to trap the capsule 5 behind the cylindrical wall of the body 63 and then further to bring the rotor 71 to the FIG. 16 configuration where the end domes of the capsule cap portion and capsule body portion have been ruptured.

Further rotation of the disc 64 to bring the rotor to the FIG. 17 configuration will suffice to prepare the device for inhalation.

At this point the mouthpiece is inserted in the mouth of a patient and the patient inhales so that the air entering through the inlet ports 66 and 81 causes a swirling motion in the inhalation chamber 77 and rotates the capsule 5 rapidly about a transverse axis, in order to eject the pulverulent medicament from the capsule by a combined centrifugal action, a suction action, and a percussive action as the capsule strikes the peripheral wall of the chamber 77.

Then, in order to prepare the device for the next use, the mouthpiece is swung aside and the spent capsule removed, following which the disc 64 is then rotated by a further 90° from the FIG. 17 position to the FIG. 15 position to bring the capsule-receiving recess 69 into register with the capsule-insertion opening 69.

Although in each of the above embodiments the first and second walls of the chamber, namely the opposed walls which together constrain the capsule or each separated capsule portion to maintain its axis of symmetry parallel to the median plane of the chamber are shown throughout as flat, it is of course possible for these walls to be other than truly flat, while still maintaining a shape sufficiently close to the flat shape for allowing the desired capsule-constraining action to be effected. Where the walls are not flat, it is the minimum spacing between these walls which is related to the dimensions of the capsule.

In the embodiment of FIGS. 1 to 6, the spacing between these first and second opposed walls defined by the rear casing panel 4 and the grid 7 is less than the axial length of the capsule body portion 5a and less than the axial length of the capsule cap portion 5b.

In the embodiments of FIGS. 7 to 9 and 10 to 12 the spacing between these first and second opposed walls is less than the total axial length of the capsule. This preferred feature guards against any possibility of the capsule becoming jammed in an oblique configuration where the roughness of the grid might assist in holding the capsule and preventing it from rotating freely in the swirling airstream.

What is claimed is:

1. An inhaler comprising a chamber defined by
   (a) first and second generally parallel spaced opposed walls defining a median plane of said chamber mid-way therebetween, said inhaler including
   (b) a capsule disposed between said parallel spaced walls, said capsule having a length greater than the space between said first and second walls and having a longitudinal axis that is generally parallel to said first and second walls in any angular orientation, said chamber having
   (c) at least one peripheral wall;
   (d) an exhaust nozzle in communication with said chamber through which inhalation air can be exhausted from said chamber by inhalation;
   (e) at least one air inlet arranged in relation to the exhaust nozzle for generating in the chamber during inhalation an airflow of inhalation air rotating about an inhalation air axis generally perpendicular to said first and second walls; and
   (f) holding means having an axis of symmetry in the inhaler in association with
   (g) opening means operable from outside the chamber when closed for opening a capsule held in the holding means, wherein, during use of the inhaler, the holding means is effective to hold said capsule having a length greater than the space between said first and second walls said holding means being configured to hold said capsule having a diameter less than said space between the first and second walls; wherein said holding means are effective to hold said capsule with its longitudinal axis perpendicular to said inhalation air axis airflow within said chamber is rotating during inhalation.

2. An inhaler according to claim 1, wherein said capsule comprises a cap portion and a body portion and said capsule opening means comprises means for physically separating the cap portion of the capsule from the body portion of the capsule whereupon said separated cap and body portions are able to tumble in the chamber during inhalation.

3. An inhaler according to claim 2, wherein the minimum spacing between said first and second walls of the chamber is less than the axial length of said capsule cap portion and less than the axial length of said capsule body portion.

4. An inhaler according to claim 1, wherein said means for opening the capsule comprises means for rupturing the capsule to permit discharge of contents of the capsule when the capsule spins in the airflow of inhalation air during inhalation, and the holding means comprise a recess configured to receive a capsule for rupturing.

5. An inhaler according to claim 4 wherein the recess extends generally peripherally outwardly from said chamber, and said rupturing means comprises means for piercing the ends of a capsule received in said recess with its longitudinal axis extending generally peripherally outwardly from the chamber, and further comprising means for ejecting a pierced capsule from said recess into the chamber.

6. An inhaler according to claim 5, wherein said ejector means includes a capsule-ejecting end face which smoothly conforms to the said at least one peripheral wall when the ejector is in a position corresponding to ejection of the capsule having been achieved.

7. An inhaler according to claim 1 wherein the exhaust nozzle is eccentric in relation to said chamber, whereby the capsule spins in the inhalation airflow thereby causing said capsule to collide against the at least one peripheral wall of said chamber.

8. An inhaler according to claim 1, wherein the capsule opening means comprises a recess extending generally peripherally outwardly from said chamber, and said rupturing means comprises means for piercing the ends of a capsule received in said recess with its longitudinal axis extending generally peripherally outwardly from the chamber, and further comprising means for ejecting a pierced capsule from said recess into the chamber.

9. An inhaler which comprises a chamber defined by (a) first and second generally parallel spaced opposed walls defining a median plane of said chamber mid-way therebetween and between which parallel spaced walls (b) a medicament-containing capsule, having a length greater than the space between said first and second walls and having a longitudinal axis and a transverse axis perpendicular to the longitudinal axis and comprising a capsule cap portion and a capsule body portion, can be received so that its longitudinal axis is generally parallel to said first and second walls in any angular orientation, and (c) at least one peripheral wall;

(d) an exhaust nozzle in communication with said chamber through which inhalation air can be exhausted from said chamber by inhalation;

(e) at least one air inlet arranged in relation to the exhaust nozzle for generating in the chamber during inhalation an airflow of inhalation air rotating about an inhalation air axis generally perpendicular to said first and second walls; and (f) a recess in the inhaler in association with (g) means for opening a closed capsule containing medicament held in the recess with the longitudinal axis of the capsule generally parallel to said first and second walls, wherein the opening means are effective to open a capsule having a length greater than the minimum spacing between said first and second walls and less than the minimum cross-sectional dimension of said chamber when viewed parallel to said axis of rotation, and to open a capsule having a diameter less than said minimum spacing between the first and second walls; said chamber being non-circular in shape and thereby providing an area in which the capsule rotates freely about its transverse axis responsive to an inhaled airstream during which rotation said capsule impacts against at least one further wall causing medicament within said capsule to be ejected therefrom.

10. An inhaler according to claim 9, wherein said means for opening the capsule comprises means for rupturing the capsule to permit discharge of contents of the capsule when the capsule spins in the airflow of inhalation air during inhalation, and said recess is configured to receive a capsule for rupturing.

11. An inhaler according to claim 6 wherein said capsule holding means receives the capsule in a position such that its longitudinal axis extends generally peripherally outwardly from of the chamber, when the capsule is being opened, whereupon the capsule is released from said holding means for extraction of capsule contents by the airflow of inhalation air.

12. An inhaler according to claim 10, wherein the minimum spacing between said first and second walls of the chamber is less than the axial length of the capsule to be held by said recess during opening by said opening means and to be spun in said chamber during inhalation.

13. An inhaler according to claim 12, wherein the minimum space between said first and second walls is less than the length of the capsule along its longitudinal axis.

14. An inhaler according to claim 9 wherein said chamber is noncircular by virtue of said recess extending generally peripherally outwardly from the chamber.

15. An inhaler according to claim 4 wherein said capsule opening means comprises a capsule-receiving rotor rotatable about an axis parallel to the median plane of said chamber, and having a capsule recess adapted to receive the capsule with its longitudinal axis parallel to the axis of rotation of said rotor, and capsule-rupturing pins carried by said rotor and driven to rupture said capsule during rotation of the rotor between a capsule-receiving position and a capsule-releasing position when the capsule is released into said chamber.

16. An inhaler according to claim 15, wherein said capsule-rupturing pins comprise bent end portions of arcuate wires at opposite ends of said rotor, with said arcuate wires extending generally around the axis of rotation of said rotor, said bent end portions being coaxial to said capsule-receiving recess, said inhaler further comprising stationary cams which engage said arcuate wires to drive the capsule-rupturing pins axially along the capsule recess.

* * * * *